United States Patent [19]

Abbott

[11] 4,298,500
[45] Nov. 3, 1981

[54] MIXED PHASE CHROMATOGRAPHIC COMPOSITIONS

[75] Inventor: Seth R. Abbott, Concord, Calif.

[73] Assignee: Varian Associates, Inc., Palo Alto, Calif.

[21] Appl. No.: 146,711

[22] Filed: May 5, 1980

[51] Int. Cl.$^3$ .............................................. B01D 15/08
[52] U.S. Cl. ...................................... 252/428; 55/386; 210/198.2; 210/198.3; 252/430
[58] Field of Search ...................... 252/182, 428, 430; 210/198.2, 198.3, 656; 55/386

[56] References Cited

U.S. PATENT DOCUMENTS

| | | | |
|---|---|---|---|
| 3,505,785 | 4/1970 | Kirkland | 55/67 |
| 3,983,299 | 9/1976 | Regnier | 428/405 |
| 4,029,583 | 6/1977 | Chang et al. | |
| 4,108,603 | 8/1978 | Regnier et al. | |
| 4,111,838 | 9/1978 | Schaeffer et al. | 210/656 |
| 4,180,383 | 12/1979 | Johnson | 424/1 |
| 4,199,330 | 4/1980 | Nestrick et al. | 55/386 |
| 4,242,227 | 12/1980 | Nestrick et al. | 55/386 |

OTHER PUBLICATIONS

"Chromosorb ®LC-7", a Technical Data Sheet of Johns-Manville Filtration and Minerals Division.
Borovansky et al., "Chromatographic Separation of Melanosomes", *J. Chromatog.*, 134, (1977), 230–234.
Shechter, "Separation of Proteins . . . ", *Anal. Biochem.*, 58, 30–38, (1974).
Regnier et al., "Glycerolpropylsilane Bonded Phases . . . ", *J. Chrom. Sci.*, 14, (1976), 316.
Darling et al., "Rapid Purification of an RNA Tumor Virus . . . ", *J. Chromatog.*, 131, (1977), 383–390.
Hiatt et al., "Treatment of Controlled Pore Glass . . . ", *J. Chromatog.*, 56, (1977), 362–364.
Haller, "Chromatography on Glass of Controlled Pore Size", *Nature*, 206, (1965), pp. 693–696.
Mizutani et al., "Adsorption of Cationic Biological Materials . . . ", *Anal. Biochem*, 83, (1977), 216–221.

*Primary Examiner*—Deborah L. Kyle
*Attorney, Agent, or Firm*—Stanley Z. Cole; Pauline A. Clarke

[57] ABSTRACT

The mixed phase packing material of this invention, enables rapid separation of multi-sited biopolymers. This separation is achieved by "tailoring" the distance between organo-silyl groups covalently bonded to the rigid support at the Angstrom distance needed for reversible separation of the biopolymers of interest and "capping" other sterically available active sites on the support with a relatively inert compound.

38 Claims, No Drawings

MIXED PHASE CHROMATOGRAPHIC COMPOSITIONS

DESCRIPTION

1. Technical Field

This invention relates to novel mixed phase compositions and, more specifically, to mixed phase compositions useful as column packing materials where an active component is covalently bonded to less than the maximum number of sterically available active sites on the support material and an inert or relatively inert component is covalently bonded to other of the available active sites on the support material, and relates to a process for making the compositions.

2. Background Art

Chromatographic columns have for many years been used for the separation of mixtures of hydrophobic, hydrophilic, or ionic organic or inorganic compounds. However, biopolymers such as peptides, proteins, oligonucleotides and nucleic acids with numerous hydrophobic or ionic sites on each molecule tend to irreversibly attach to a chromatograhic column material whose stationary phase can sorb such hydrophobic or ionic groups. This adsorption phenomenon has led to the development of numerous column packing materials for the separation of multiple-sorbable-sited compounds. Adsorption is a strong interaction between a molecule and the packing material which requires the use of a strong or harsh solvent (mobile phase) to break the molecule-packing material interaction and allow elution of the molecule. In cases where the interaction is irreversible, no solvent, even a strong or harsh one, will enable elution of the molecule without degrading the packing material and/or the molecule.

Classical steric exclusion separations of biopolymers have utilized relatively soft, hydrophilic gels such as the synthetic polyacrylamides (example, Bio-Gel P) and the polysaccharide dextrans (for example, Sephadex) and agaroses (for example, Sepharose, Bio-Gel A).

Unfortunately, these hydrophilic gels are characterized by a relatively low compressive strength and must be operated at low pressures and flow velocities. Thus, equilibration, separation and washing times are long and sample throughput is low. Cross-linked agarose, the most mechanically stable of these gels, and the support used by J. Borovansky, P. Hach and J. Duchon, *J. Chromatogr.*, 134, 230 (1977) to separate melanosomes, subnuclear particles, is generally operated at flow velocities of about 0.002 to about 0.02 cm/sec. This is an order of magnitude slower than typical high speed liquid chromatography flow velocities.

Rigid microparticulate supports such as the controlled-porosity glasses developed by Haller [W. Haller, *Nature* 206, 693 (1965)] have been used for steric exclusion of biopolymers of molecular weights up to $10^6$. However, controlled-pore glasses (as well as silica gel) are characterized by high densities of highly polar, weakly acidic silanol (Si-OH) groups. Silanols can behave as cation exchange sites and result in adsorption and denaturation of biopolymers [T. Mizutani and A. Mizutani, *Anal. Biochem,* 83, 216 (1977); C. W. Hiatt, A. Shelokov, E. J. Rosenthal and J. M. Galimore, *J. Chromatogr.*, 56(2), 362 (1971)], especially proteins with isoelectric points above pH 7.5. A column packed with dry glass powder treated with γ-aminopropyltriethoxysilane [Hiatt, et al.] was used to elute poliovirus; however, rabies virus with active group spacings different from those of poliovirus was either totally absorbed or inactivated under these conditions.

Coating of controlled-pore glass and silica gel supports with polyethylene glycol was found to significantly reduce biopolymer adsorption effects [T. Darling, J. Albert, P. Russell, D. M. Albert, and T. W. Reid, *J. Chromatogr.*, 131, 383 (1977)]. However, the coating process was reversible (column "bleed" occurred) and the polyethylene glycol phase eluted under continuous use [I. Shechter, *Anal. Biochem.*, 58, 30 (1974)].

This glycol coating "bleed" problem was overcome by covalently bonding the hydrophilic phase onto all of the available hydroxyl groups of controlled-pore glass or silica gel supports. My copending applications, Ser. No. 953,380, filed Oct. 23, 1978; Ser. No. 16,847, filed Mar. 2, 1979; and Ser. No. 112,964, filed Jan. 17, 1980, describe the use of aqueous solutions for covalently bonding active phases to all of the sterically available silica hydroxyl groups. In these copending applications the reaction is carried out near room temperature without pH adjustment using an amine-containing alkoxysilane such as N-2-aminoethyl-3-aminopropyltrimethoxysilane or N-trimethoxysilylpropyl-N,N,N-trimethylammonium chloride.

A "diol" phase (γ-glycidoxypropyl-) has been bonded onto all of the sterically available hydroxyl groups of both controlled-pore glasses [F. Regnier and R. Noel, *Journal Chromatogr. Sci.,* 14, 316 (1976)] and microparticulate silica gel [S. H. Chang, K. M. Gooding, and F. E. Regnier, *Journal Chromatogr.*, 125 103 (1976)], by using aqueous acidic (pH 3.5) solutions of the diol at elevated temperatures (90° C.). The resulting "glycophases" yielded good steric exclusion column packing materials for the separation of proteins, polynucleotides and polysaccharides. However, they were not designed for separation according to the reactive site spacings of the biopolymers of interest.

Polydextran has also been bonded onto all of the available hydroxyl groups on silica through an alkylamine, amide, or isourea intermediary (F. E. Regnier, U.S. Pat. No. 3,983,299) to yield a mechanically stable support with little adsorption or denaturation of some sensitive biological compounds. However, enzyme recoveries from these dextran-silica supports were found to be significantly lower (due to adsorption) than those obtained from the diol-silica supports and again were not designed for separation according to the reactive site spacings of the biopolymers of interest.

An ion exchange group has been bonded onto all of the glycerol moieties of a glycerol-silica to form a "piggyback" high speed chromatographic support useful for high speed chromatographic analysis of some biological macromolecules by hydrophobic and ion exchange partitioning [S. Chang, K. Gooding and F. Regnier, *J. Chromatogr.*, 125, 103 (1976); F. Regnier, U.S. Pat. No. 4,029,583]. This piggyback composition was prepared by reacting an aqueous (acidic pH) solution of a carbohydrate or carbohydrate derivative or a polymer (e.g., γ-glycidoxypropyltrimethoxysilane, γ-GP) with all of the reactive hydroxyl groups of a support matrix such as a controlled-pore glass or silica gel at elevated temperature (90° C.), followed by reflux of the product for about 18 hours with an amine (e.g., diethylaminoethanol, DEAE) in dimethylformamide.

For improved separation (to overcome adsorption or elution without separation) of hemoglobin variants, γ-glycidoxypropyltrimethoxysilane has been bonded, Regnier, U.S. Pat. No. 4,108,603, onto all of the reactive hydroxyl groups of a controlled-pore glass using an aqueous (acidic) solution at elevated temperature, followed by reflux addition of diethylaminoethanol onto all of the glycidoxypropyl groups using a mixture of triglycidylglycerol, and diethylaminoethanol. This step was followed by a second addition of triglycidoxyglycerol using boron trifluoride to form a polymerized fluidized bed.

A packing material composition, Chromosorb® LC-7, marketed by Johns-Manville Filtration and Materials Division, contains a monomolecular layer of octadecyl groups bonded by Si-C linkages to 15% of the available surface hydroxyls. This composition is prepared by the proprietary reaction of an organochlorosilane with the surface hydroxyls of a microparticulate silica. There is no indication that the other surface active hydroxyls are reacted with a second residue.

Thus the prior art can rapidly separate given biopolymers by using chromatographic column packings which have varied pore size, can withstand the pressures normally associated with HPLC, can tolerate high flow velocities, and do not compress with time. However, prior art column packing materials of which I am the inventor have not been designed specifically to contain both reactive and non-reactive groups each covalently bonded to the support at distances specific for separation of biopolymers classed according to the spacing of the hydrophobic or ionic sites along their length without adsorption or degradation, and the prior art of which I am aware fails to provide a process for the preparation of such materials.

Disclosure of the Invention

It is accordingly one object of the present invention to provide a novel mixed phase composition that is tailored to rapidly separate multiple-sorbable-sited polymers.

A further object is to provide a novel mixed phase composition which is capable of rapid elution of multiple-sorbable-sited biopolymers such as tRNA.

A still further object of this invention is to provide a mixed phase composition having this capability that utilizes a "gentle" mobile phase.

An even further object is to provide a novel process for preparing the mixed phase composition.

Other objects and advantages will become apparent as the description proceeds.

In satisfaction of the foregoing objects and advantages, there is provided by the present invention a mixed phase composition that is comprised of a porous particle suitable for use in chromatography, a first residue capable of separating multiple-sorbable-sited compounds covalently bonded to less than the maximum number of sterically available porous particle active sites, and a second residue inert or relatively inert to the multiple-sorbable-sited compounds and covalently bonded to other of the sterically available porous particle active sites. The first and second residues are directly attached to the active sites.

This invention also provides a process for the manufacture of this mixed phase composition. This process includes the steps of (a) degassing the particle, (b) reacting the reagent from which the first residue is formed with an aqueous slurry of the degassed particle at a time and temperature sufficient to produce a product having the first residue covalently bonded to the particle, (c) reacting a degassed aqueous slurry of the product of step (b) with the reagent from which the second residue is formed at a time and temperature sufficient to produce a product having the second residue covalently bonded to the particle at sterically available porous particle sites other than those occupied by the first residue, and (d) recovering the mixed phase composition of the present invention. The particle is present in step (b) in a stoichiometric excess, the excess being that of the active sites of the particle to the first reagent, whereby less than the maximum number of sterically available porous particle active sites are bonded by the first residue.

Best Mode for Carrying Out the Invention

Nucleic acids are known to have several ionic sites (phosphate groups) spaced approximately 8 Angstroms apart. Proteins on the other hand, are known to have their ionic sites spaced further apart. Such variation in the spacing of ionic groups makes separation on silica gel-based columns difficult. Chromatographic grade silicas contain surface silanol (—Si—OH) groups spaced approximately every 5 Angstroms. A typical anhydrous reaction of this silica with an organosilane group-containing reagent, in which the silane is in excess (2–10 fold) relative to the silanol level, results in reaction of only 25–50% of the active sites on the silica since further reaction is inhibited by steric hindrance. Thus, the resultant silica-based organic bonded phase material contains organic phase sites spaced every 10 to 20 Angstroms.

When a solution of a biopolymer containing hundreds of anion sites spaced every 10 Angstroms is injected onto a column packed with a silica-based material containing organic anion exchange sites spaced every 10 Angstroms, hundreds of bonds are formed between the material and the biopolymer. Thus, elution of the biopolymer is difficult, if not impossible, and requires an extremely potent or harsh mobile phase.

This difficulty is overcome by the present invention which provides in a first embodiment a mixed phase composition. This composition is made of a porous particle suitable for use in chromatography, to less than the maximum number of sterically available active sites of which there is covalently bonded a first residue according to this invention, as a result of which the first residues are spaced more than about 20 Angstroms apart. Less than the maximum number of sterically available active sites is bonded by reacting the particle with an amount of a first residue-forming reagent that is stoichiometrically less, on a molar basis, than the amount of sterically available active sites. An about 10 to 1 mole ratio of sterically available active sites, in the case of silica as the particle, to the first residue-forming reagent produces a composition in which the organic sites are spaced about every 50 Angstroms. Similarly, an about 50 to 1 mole ratio of sterically available active sites, in the case of the silica, to the first residue-forming reagent produces an organic phase site spacing of about 250 Angstroms. Thus, this composition is capable of being tailored to the type of biopolymer to be separated. This composition allows chromatography of multiple-sorbable-sited compounds such as polyvalent site or hydrophobic site biopolymers with "gentle" mobile phases since there is not a strong interaction of the biopolymer with the packing composition.

An excess of sterically available active sites to the reagent from which the first residue is formed ranging, on a molar basis, from about 10-50:1 is particularly advantageous in forming the mixed phase composition of the present invention. Similarly, a mixed phase composition having the first residues spaced from about 50 to 250 Angstroms apart is especially suitable. However, any excess ratio of the sites to the first residue-forming reagent is useful, with the selection of the precise ratio being determined by the multiple-sorbable-sited compound to be separated. In this manner, the mixed phase composition is tailored with respect to the spacing between the first residues.

This mixed phase composition also is made of a second residue which is inert or relatively inert to the multiple-sorbable-sited compound being separated, which is illustratively a biopolymer. The second residue advantageously provides steric exclusion but no adsorption or ion exchange effects. Illustratively, the second residue is provided by a hydrophilic phase such as an organosilane-containing diol, diol precursor or amide. The second residue is bonded to some or all of the residual sterically available active sites of the particle. The porous particle preferably has a size in the range of from about 5 to about 20 microns, with a pore size in the range from about 100 to 4000 Angstroms. Silica is preferred, and a high performance liquid chromatography (HPLC) grade silica gel is a particularly preferred type of silica. An HPLC grade silica gel having a high surface area, i.e., about 5 to 250m$^2$/g, a pore diameter of about 100 to 4000 Angstroms, and a size of about 5 to about 20 microns is an especially suitable type of silica gel. A silica gel of this type is commercially available as 10 micron Lichrospher ® Si-500, sold by Merck, Inc. However, any chromatography grade wide-pore silica gel is suitable. It should be noted that as pore size increases, particle fragility increases. Wide-pore silicas such as Lichrospher ® are characterized by pressure limits of 4000 psi.

The first residue is capable of separating multiple-sorbable-sited compounds. Suitably, the first residue is formed from an organosilane group-containing reagent. This reagent is advantageously a weak anion exchange reagent, a strong anion exchange reagent, a weak cation exchange reagent, a strong cation exchange reagent, or a reverse phase reagent, with a weak anion exchange reagent being particularly advantageous.

An exemplary weak anion exchange reagent has the general formula:

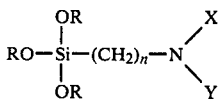

wherein n is an integer ranging from 2-5; R is methyl or ethyl; and X and Y are methyl or ethyl, with X and Y being the same or different. This reagent has an organic coupling group [e.g, (CH$_2$)$_n$] to the silicon which has minimal reverse phase character. Thus, the n number is most advantageously 2 or 3 to prevent any reverse phase character associated with longer carbon chains. Illustratively, this reagent is N,N-diethylaminopropyl-trimethoxysilane, available from Petrarch Systems, Inc. Other weak anion exchange reagents are disclosed in my pending U.S. application Ser. No. 16,847, filed Mar. 2, 1979, the pertinent disclosure of which is hereby incorporated by reference into this application.

An exemplary strong anion exchange reagent is an ammonium compound having the general formula:

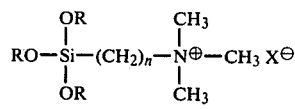

wherein n is an integer ranging from 2-5; R is methyl or ethyl; and X is an exchangeable anion such as a chloride anion and a phosphate anion. Illustratively, this reagent is N-trimethoxysilypropyl-N,N,N-trimethylammonium chloride, available from Petrarch Systems, Inc. This compound is further disclosed in my pending U.S. application Ser. No. 112,964, filed Jan. 17, 1980, and the pertinent portions of this disclosure are hereby incorporated by reference into this application.

As explained above, the second residue is illustratively provided by a hydrophilic phase that is suitably an organosilane-containing diol, diol precursor or amide. An especially suitable diol has the following general structure:

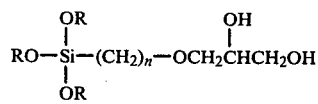

wherein R is methyl or ethyl, and n is an integer ranging from 2-5. An especially suitable diol precursor has the general formula:

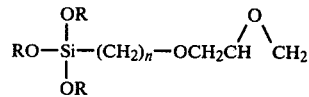

wherein R is methyl or ethyl, and n is an integer ranging from 2-5. This diol precursor is, for example, γ-glycidoxypropyltrimethoxysilane, available from Petrarch Systems, Inc., which upon further reaction is converted from an oxirane to a diol. An especially suitable amide has the general formula:

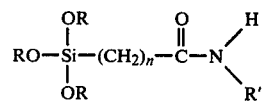

wherein n is an integer ranging from 2-5; R is methyl or ethyl, and R' is methyl or ethyl. This amide, for example, is N-(3-triethoxysilylpropyl)acetamide, which is prepared by reacting 3-aminopropyltriethoxysilane with acetic anhydride according to the method of Engelhardt [H. Engelhardt and D. Mathes, Journal Chromatogr., 142, 311 (1977)].

In the preferred silica-containing mixed phase composition, the relatively hydrophobic organic center portions of the composition provide protection to the silica inner portion against gradual attack by an aqueous solvent by shielding the silica from the aqueous solvent. Also, with the prepared silica-containing embodiment of the mixed phase composition, some of the charged polar silanol groups are eliminated from the silica surface by tying these groups to a covalent bond (those silanol groups not so eliminated do not react with the biopolymers being separated because of steric hindrance of the covalently bonded residues). The elimination of the disadvantages associated with silica avoids the adsorption and clogging problems experienced with prior art coated or bare porous particle compositions.

The present invention provides in a second embodiment a process for the manufacture of the mixed phase composition wherein less than the maximum number of sterically available porous particle active sites are reacted to form covalent bonds with the first reagent, and other sterically available active sites are reacted with the second reagent.

In the initial step of preparation of this mixed phase composition, the reagent from which the first residue is formed, e.g., N,N-diethylaminopropyltrimethoxysilane (DEAPTMS) is reacted with a degassed aqueous slurry of the porous particle. Degassing is by conventional means. This reaction is conducted for a time and at a temperature sufficient to covalently bond the first residue to the sterically available active sites of the particle. Suitably, the time is about 15 minutes to 24 hours, and the temperature is from about 20° to about 50° C. The aqueous slurry is prepared, for example, using about 5 to about 15% by weight of the particle, preferably about 10% by weight. The aqueous solvent is advantageously water. The choice of solvent and of reaction conditions is very important since proper selection, as discussed above, provides an unpolymerized reaction product.

As explained above, selection of the molar proportion of sterically available active particle sites to the reagent from which the first residue is formed enables the resultant mixed phase composition to be tailored to the biopolymer being separated. In the present process, the active sites are provided in stoichiometric excess, on a molar basis, as a result of which less than the maximum number of sites are bonded by the first residue. To prepare a mixed phase composition with only about 10% of the available sites, in the case of silica, reacted with the first residue-forming reagent, which is illustratively DEAPTMS, about 0.1 milliliter of DEAPTMS is advantageously combined with about 10 grams of silica. Other amounts of the reagent are used to prepare other mixed phase compositions with slightly less or more coverage of the silica silanols by the reagent residue.

The product of the first reaction is recovered, washed and dried. Recovery is advantageously carried out by filtering the resulting slurry of this reaction. Suitably, the slurry is filtered through a sintered glass funnel having a pore size smaller that the particle size, and the product is recovered as a filter cake. The filter cake is washed using a series of solvents to remove solvent-soluble impurities. An advantageous series of solvents comprises water, methanol, tetrahydrofuran and then methanol again. About 100-500 milliliters of each of these solvents is suitably used in the washing for each 10 grams of the particle. Then the filter cake is dried according to conventional procedures.

In the next step of this procedure, an aqueous solution of the "capping" reagent, e.g. $\gamma$-glycidoxypropyltrimethoxysilane ($\gamma$-GP) is prepared. Suitably, an amount of $\gamma$-GP is added to an aqueous solvent to form an about 10% solution. The aqueous solvent is advantageously water. The addition, for example, is at about room temperature by dropwise addition of the $\gamma$-GP to the aqueous solvent while maintaining the pH between about 5 and 6. The resulting solution is degassed for advantageously about 2 minutes with swirling using hand or mechanical mixing. To the degassed solution there is added the product of the previous reaction. The resulting slurry is reacted for a time and at a temperature sufficient to covalently bond the capping reagent directly to some of all of the residual sterically available porous particle active sites. Suitably, the slurry is refluxed at approximately 100° C. for about 2 hours.

This product is recovered, washed and dried. Recovery is advantageously carried out by filtering the resulting slurry of the preceding step. Suitably, the slurry is filtered through a sintered glass funnel having a pore size smaller than the particle size, and the product is recovered as a filter cake. The filter cake is washed using a series of solvents to remove solvent-soluble impurities. An advantageous series of solvents comprises water, methanol, tetrahydrofuran and then methanol again. About 200-600 milliliters of each of these solvents is suitably used in the washing for each 10 grams of the particle. Then the filter cake is dried according to conventional procedures.

When a diol precursor such as $\gamma$-GP is used as the capping reagent, an additional step is required. In this step, the diol precursor-containing product of the previous step is hydrolyzed to form the diol. Suitably, this is done by stirring the precursor-containing product at about room temperature in a dilute aqueous acid solution. An advantageous method for this step, when there are about 10 grams of this product, is to stir the product in about one liter of 0.01 M $HNO_3$ for about 1 to about 3 hours at room temperature, with about 2 hours being preferred.

This diol-containing particle is then recovered, washed and dried. Recovery is advantageously carried out by filtering the resulting slurry of the preceding step. Suitably, the slurry is filtered through a sintered glass funnel having a pore size smaller than the particle size, and the product is recovered as a filter cake. The filter cake is washed with water until the pH of the wash water is approximately 6. The filter cake is then washed with approximately 250 milliliters of methanol (per 10 grams of the particle) to remove solvent-soluble impurities. The filter cake is then dried according to conventional procedures. The dried product is then slurried with an appropriate packing solvent such as methanol, and packed into the column at elevated pressure according to conventional procedures.

Methods of Use

The mixed phase composition of the present invention is useful for the separation of multiple-sorbable-sited biopolymers. With "tailoring", that is variation of the Angstrom spacing of the reactive groups bonded to the sterically available active sites, and "capping" of other sterically available active sites, the composition of the present invention is designed for separation of specific biopolymers. That is, a reactive group spacing of about 35 Angstroms is useful for rapid separation of nucleic acid components while proteins may be unretained and thus not separated on the same matrix. A mixed phase composition designed with a reactive group spacing enabling rapid separation of proteins, may irreversibly retain a mixture of nucleic acid components. Thus, while the examples given are for a specific reactive group spacing, many different spacings can be used with the reactive groups filling 25% or less of the active sites available. It should be realized that a 25-50% coverage is maximum in the case of a particle such as silica.

The below examples are illustrative of the present invention. It is to be understood that these examples are not in any way to be interpreted as limiting the scope of the invention. Unless otherwise indicated, all percentages are by weight.

EXAMPLE I

Preparation of the Chromatographic Composition (a) A slurry in 100 ml distilled water of 10 grams of Lichrospher ® Si-500, available from Merck, Inc. is prepared and then degassed in an ultrasonic bath for 5 minutes using a water aspirator. To the degassed slurry there is added 0.1 ml of N, N-diethylaminopropyltrimethoxysilane (DEAPTMS, sold by Petrarch Systems, Inc.). The reaction vessel is capped, and the reaction is allowed to proceed for 2.5 hours at room temperature. The reaction product is then filtered on a medium sintered glass filter funnel, and there is recovered on the funnel as a filter cake the weak anion exchange group (N,N-diethylaminopropylsilyl-) covalently bonded to less than the maximum number of sterically available silica silanols. The filter cake is washed with each of the following solvents, in turn : 100 ml water, 200 ml methanol, 200 ml tetrahydrofuran, and 200 ml methanol. The washed cake is then dried.

(b) A solution in 100 ml distilled water of γ-glycidoxyprop yltrimethoxysilane (γ-GP, sold by Petrarch Systems, Inc.), is prepared by dropwise addition of 10 ml of γ-GP to the water. During addition of γ-GP, the pH of the solution is maintained between 5 and 6 by addition of 0.01 M KOH.

(c) A slurry of the γ-GP solution of step (b) with the reaction product of step (a) is prepared and then degassed in an ultrasonic bath for 2 minutes using a water aspirator. A reflux condenser and magnetic stirrer are then attached to the slurry flask and the slurry is refluxed for 2 hours. The reaction product is then filtered on a medium glass filter funnel, and there is recovered on the funnel as a filter cake the weak anion exchange-diol-precursor-silica reaction product. The filter cake is washed with each of the following solvents, in turn: 500 ml water, 250 ml methanol, 200 ml tetrahydrofuran, and 250 ml methanol. The washed cake is then dried.

(d) A slurry of the weak anion exchange-diol-precursor-silica product of step (c) in one (1) liter of 0.01 M $HNO_3$ is prepared and then stirred for 2 hours. The reaction product is then filtered on a medium sintered glass filter funnel to form a filter cake. The filter cake is washed with distilled water until the wash water is pH 6. The filter cake is then washed with 250 ml methanol and dried. The resulting product is silica to which is covalently bonded both N, N-diethylaminopropylsilyl groups and glyceropropylsilyl groups.

Silica contains 0.33 millimoles of silanols per gram. Using the proportions shown above, the N,N-diethylaminopropylsilyl coverage is less than or equal to one (1) site out of 0.3 to 0.35 or approximately one (1) DEAP per 6.6 silanol sites (this equivalent to approximately one DEAP site per 35 Angstroms).

EXAMPLE II

Elution of tRNA Standards

A 5% slurry of the diol/DEAP-silica produced in Example I in a methanol-carbon tetrachloride (1:1 by volume) solvent system is packed in a 4 mm ×30 cm column at a packing pressure of less than or equal to 4,000 psi (the pressure limit of the wide-pore silica Lichrospher ® materials). The packed column is washed with 200 ml methanol. The column is stored with methanol. However prior to use it is washed with water followed by the appropriate buffer solution for the compounds being separated. For the elution of tRNA standards the appropriate buffer is 0.1 M Tris, pH 6.8 [Tris=tris (hydroxymethyl) aminoethane].

To this column, there is added a mixture of tRNA standards, namely N-formyl-methionine tRNA and tyrosine tRNA. Using a procedure no greater than 4000 psi, the column is eluted with a solvent gradient of solvent A—0.1 M Tris, pH 6.8; solvent B—0.1 M Tris, pH 6.8 +1 M NaCl; gradient—0% B for 5 minutes then 0–45% B in 15 minutes at a flow rate of 1.0 milliliter per minute and a temperature of 30° C. The tRNA standards are eluted within 14 minutes.

EXAMPLE III

Separation of Rabbit Liver tRNA Extract

To the column of Example II, a rabbit liver tRNA extract [extract prepared according to the procedure of M. P. J. Spurgeon Anandaraj and B. A. Roe, *Biochemistry* 14, 5068 (1975)] is added. The column is eluted with a solvent gradient of: solvent A-0.1 M Tris, pH 6.8; solvent B-0.1 M Tris, pH 6.8+1 M NaCl; gradient-0%B for 5 minutes, then 0–45% in 15 minutes at a flow rate of 0.5 milliliters per minute and a temperature of 30° C. The tRNA extract components are eluted within 20 minutes.

I claim:

1. A mixed phase composition comprising a porous particle suitable for use in chromatography having a first residue covalently bonded, to less than the maximum number of sterically available support matrix active sites, said first residue being capable of separating multiple-sorbable-sited compounds, said particle also having a second residue covalently bonded to other of the sterically available support matrix active sites, said second residue being inert or substantially inert to said compounds; said first and second residues being directly attached to said active sites.

2. The mixed phase composition of claim 1 wherein said porous particle is silica.

3. The mixed phase composition of claim 2 wherein said silica is a high performance liquid chromatography grade silica.

4. The mixed phase composition of claim 3 wherein said silica has a particle size of about 5 to about 20 microns and a pore size of about 100 to 4000 Angstroms.

5. The mixed phase composition of claim 1 or 2 wherein said first residue is formed from an organosilane group-containing reagent, said reagent being a weak anion exchange reagent, a strong anion exchange reagent, a weak cation exchange reagent, a strong cation exchange reagent, or a reverse phase reagent.

6. The mixed phase composition of claim 5 wherein said first residue is formed from a weak anion exchange reagent.

7. The mixed phase composition of claim 6 wherein said weak anion exchange reagent has the general formula:

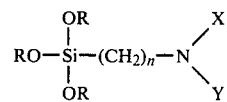

wherein n is an integer ranging from 2–5; R is methyl or ethyl; and X and Y are methyl or ethyl, with X and Y being the same or different.

8. The mixed phase composition of claim 7 wherein said weak anion exchange reagent is N, N- diethylaminopropyltrimethoxysilane.

9. The mixed phase composition of claim 1 wherein said first residue is bonded to less than 25% of said active sites.

10. The mixed phase composition of claim 1 or 2 wherein said second residue is formed from an organosilane group-containing reagent, said reagent being a diol, a diol precursor or an amide.

11. The mixed phase composition of claim 10 wherein said second residue is formed from a diol having the general formula:

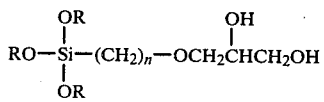

wherein n is an integer ranging from 2–5; and R is methyl or ethyl.

12. The mixed phase composition of claim 10 wherein said second residue is formed from a diol precursor.

13. The mixed phase composition of claim 10 wherein said second residue is formed from a diol precursor having the general formula:

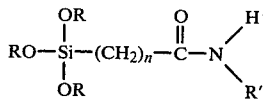

wherein n is an integer ranging from 2–5; and R is methyl or ethyl.

14. The mixed phase composition of claim 13 wherein said diol precursor is γ-glycidoxypropyltrimethoxysilane.

15. The mixed phase composition of claim 10 wherein said second residue is formed from an amide.

16. The mixed phase composition of claim 15 wherein said amide has the general formula:

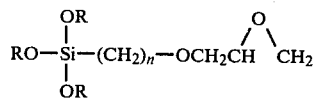

wherein n is an integer ranging from 2–5; R is methyl or ethyl, and R' is methyl or ethyl.

17. The mixed phase composition of claim 16 wherein said amide is N-(3-triethoxysilylpropyl)acetamide.

18. A process for the manufacture of a mixed phase composition comprising a porous particle suitable for use in chromatography having a first residue covalently bonded, to less than the maximum number of sterically available support matrix active sites, said first residue being capable of separating multiple-sorbable-sited compounds, said particle also having a second residue covalently bonded to other of the sterically available support matrix active sites, said second residue being inert or substantially inert to said compounds; said first and second residues being directly attached to said active sites;

said process comprising the steps of:

(a) degassing said particle, (b) reacting the reagent from which said first residue is formed with an aqueous slurry of said degassed particle at a time and temperature sufficient to covalently bond said first residue to said active sites; said particle being present in a stoichiometric excess, said excess being that of said active sites of said particle to said reagent, whereby less than the maximum number of sterically available porous particle active sites are bonded by said first residue;

(c) reacting the product of the previous step with the reagent from which said second residue is formed, in a degassed aqueous slurry at a time and temperature sufficient to covalently bond said second residue directly to other of the sterically available porous particle active sites; and (d) recovering said mixed phase composition.

19. The process according to claim 18 wherein said particle is a high performance liquid chromatography grade silica.

20. The process according to claim 18 wherein the reaction of step (b) is carried out at about 20° C. to 50° C. for a period of from about 15 minutes to about 24 hours.

21. The process according to claim 18 wherein the reaction of step (c) is carried out at reflux temperature for a period of from about 1 hour to about 4 hours.

22. The process according to claim 19 wherein said silica has a particle size of from about 5 to about 20 microns and a pore size of about 100 to 4000 Angstroms.

23. The process according to claim 18 or 19 wherein said first residue is formed from an organosilane group-containing reagent, said reagent being a weak anion exchange reagent, a strong anion exchange reagent, a weak cation exchange reagent, a strong cation exchange reagent, or a reverse phase reagent.

24. The process according to claim 23 wherein said first residue is formed from a weak anion exchange reagent.

25. The process according to claim 24 wherein said weak anion exchange reagent has the general formula:

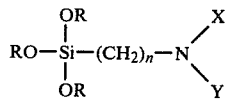

wherein n is an integer ranging from 2–5; R is methyl or ethyl; and X and Y are methyl or ethyl, with X and Y being the same or different.

26. The process according to claim 25 wherein said weak anion exchange reagent is N,N-diethylaminopropyltrimethoxysilane.

27. The process according to claim 18 or 19 wherein said second residue is formed from an organosilane group-containing reagent, said reagent being a diol, a diol precursor, or an amide; provided that if the residue is formed from the diol precursor, the process further comprises hyrolyzing the product of step (c) to form a diol.

28. The process according to claim 27 wherein said second residue is formed from a diol having the general formula:

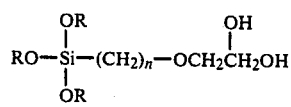

wherein n is an integer ranging from 2–5; and R is methyl or ethyl.

29. The process according to claim 27 wherein said second residue is formed from a diol precursor.

30. The process according to claim 29 wherein said second residue is formed from a diol precursor having the general formula:

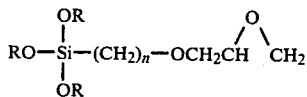

wherein n is an integer ranging from 2–5; and R is methyl or ethyl.

31. The process according to claim 30 wherein said diol precursor is γ-glycidoxypropyltrimethoxysilane.

32. The process according to claim 27 wherein said second residue is formed from an amide.

33. The process according to claim 32 wherein said amide has the general formula:

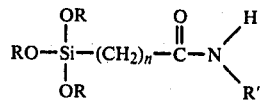

wherein n is an integer ranging from 2–5; R is methyl or ethyl, and R' is methyl or ethyl.

34. The process according to claim 33 wherein said amide is N-(3-triethoxysilylpropyl) acetamide.

35. The process according to claim 18 wherein the sterically available active sites of the particle range from about 10–50:1, on a molar basis, relative to the reagent from which the first residue is formed.

36. The process according to claim 18 wherein said multiple-sorbable-sited compound is a biopolymer.

37. The process according to claim 36 wherein said biopolymer is a nucleic acid.

38. The process according to claim 37 wherein said nucleic acid is transfer-RNA.

* * * * *